(12) United States Patent
Li et al.

(10) Patent No.: US 9,255,099 B2
(45) Date of Patent: Feb. 9, 2016

(54) PYRAZOLO[3,4-D]PYRIMIDINE-4,6(5H,7H)-DIONES AS PHOSPHODIESTERASE 1 INHIBITORS

(75) Inventors: Peng Li, New York, NY (US); Lawrence P. Wennogle, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 1002 days.

(21) Appl. No.: 12/303,618

(22) PCT Filed: Jun. 6, 2007

(86) PCT No.: PCT/US2007/070551
§ 371 (c)(1),
(2), (4) Date: Dec. 5, 2008

(87) PCT Pub. No.: WO2007/143705
PCT Pub. Date: Dec. 13, 2007

(65) Prior Publication Data
US 2010/0173878 A1    Jul. 8, 2010

Related U.S. Application Data

(60) Provisional application No. 60/811,687, filed on Jun. 6, 2006, provisional application No. 60/873,185, filed on Dec. 5, 2006.

(51) Int. Cl.
| | |
|---|---|
| C07D 487/04 | (2006.01) |
| A61K 31/519 | (2006.01) |
| A61P 11/06 | (2006.01) |
| A61P 13/08 | (2006.01) |
| A61P 15/00 | (2006.01) |
| A61P 19/10 | (2006.01) |
| A61P 25/16 | (2006.01) |
| A61P 25/18 | (2006.01) |
| A61P 25/22 | (2006.01) |
| A61P 25/28 | (2006.01) |
| A61P 25/30 | (2006.01) |
| A61P 37/00 | (2006.01) |
| A61P 37/08 | (2006.01) |
| A61P 9/10 | (2006.01) |

(52) U.S. Cl.
CPC .................. C07D 487/04 (2013.01)

(58) Field of Classification Search
CPC ............................ C07D 487/04; A61K 31/519
USPC ........................................ 544/262; 514/262.1
See application file for complete search history.

(56) References Cited

U.S. PATENT DOCUMENTS

| | | |
|---|---|---|
| 3,689,863 A | 9/1972 | Matsuoka et al. |
| 3,993,650 A | 11/1976 | Tarzia et al. |
| 4,663,326 A | 5/1987 | Hamilton et al. |
| 4,824,848 A * | 4/1989 | Naka et al. ............... 514/262.1 |
| 5,202,328 A | 4/1993 | De Laszlo et al. |
| 5,223,501 A | 6/1993 | Chakravarty et al. |
| 5,294,612 A | 3/1994 | Bacon et al. |
| 5,393,755 A | 2/1995 | Neustadt et al. |
| 5,409,934 A | 4/1995 | Smith et al. |
| 5,719,283 A | 2/1998 | Bell et al. |
| 5,939,419 A | 8/1999 | Tulshian |
| 6,133,273 A | 10/2000 | Gilbert et al. |
| 6,166,019 A | 12/2000 | Meyer et al. |
| 6,235,742 B1 | 5/2001 | Bell et al. |
| 6,492,371 B2 | 12/2002 | Roylance |
| 6,756,373 B1 | 6/2004 | Allerton et al. |
| 7,153,824 B2 | 12/2006 | Palmer et al. |
| 7,157,451 B2 | 1/2007 | Atwal et al. |
| 2003/0092908 A1 | 5/2003 | Pitts et al. |
| 2003/0162782 A1 | 8/2003 | Grossman et al. |
| 2004/0254183 A1 | 12/2004 | Basarab et al. |
| 2005/0048573 A1 | 3/2005 | Artis et al. |
| 2005/0075795 A1 | 4/2005 | Pandit |
| 2006/0160831 A1 | 7/2006 | Tsutsumi et al. |
| 2006/0252790 A1 | 11/2006 | Allen et al. |

(Continued)

FOREIGN PATENT DOCUMENTS

| | | |
|---|---|---|
| DE | 197 09 126 | 3/1997 |
| DE | 199 31 206 | 1/2001 |

(Continued)

OTHER PUBLICATIONS

Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
Lugnier et. al. (Pharmacology & Therapeutics, 2006, 109, pp. 306-398).*
Morgan (Expert Opinion, 2006, 11(3), 403-417).*
Medina (Frontiers in Neuroscience, 2011, 5, pp. 21).*
Ahn, H. et al., "Potent Tetracyclic Guanine Inhibitors of PDE1 and PDE5 Cyclic Guanosine Monophosphate Phosphodiesterases with Oral Antihypertensive Activity", J. Med. Chem., 1997, 40(14), pp. 2196-2210.

(Continued)

Primary Examiner — Susanna Moore
(74) Attorney, Agent, or Firm — Hoxie & Associates LLC

(57) ABSTRACT

2-(optionally hetero)arylmethyl-3-(optionally hetero)arylamino-[2H]-pyrazolo[3,4-d]pyrimidine-4,6(5H, 7H)-diones, for example, a compound of Formula I:

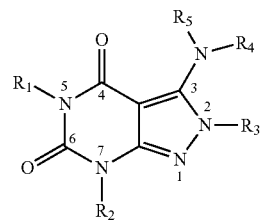

in free, salt or prodrug form, are useful as pharmaceuticals, particularly as phosphodiesterase 1 inhibitors.

29 Claims, No Drawings

(56) References Cited

U.S. PATENT DOCUMENTS

| | | |
|---|---|---|
| 2007/0208029 A1 | 9/2007 | Barlow et al. |
| 2008/0176961 A1 | 7/2008 | Greengard et al. |
| 2008/0188492 A1 | 8/2008 | Li et al. |
| 2008/0194592 A1 | 8/2008 | Mates et al. |
| 2009/0137549 A1 | 5/2009 | Edward et al. |
| 2010/0087450 A1 | 4/2010 | Fienberg et al. |
| 2010/0273753 A1 | 10/2010 | Li et al. |
| 2010/0273754 A1 | 10/2010 | Li et al. |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li et al. |

FOREIGN PATENT DOCUMENTS

| | | |
|---|---|---|
| EP | 0 063 381 | 10/1982 |
| EP | 0166054 | 1/1986 |
| EP | 0 201 188 | 12/1986 |
| EP | 0237289 | 9/1987 |
| EP | 0 306 185 | 8/1988 |
| EP | 0 353 941 | 7/1989 |
| EP | 0 383 465 | 2/1990 |
| EP | 0 911 333 | 4/1999 |
| EP | 1 097 706 | 11/2000 |
| EP | 1852108 | 11/2007 |
| JP | 53031694 | 3/1978 |
| JP | 01265027 | 4/1988 |
| JP | 02289518 | 11/1990 |
| KR | 10-1991-0006866 | 9/1991 |
| NL | 1 186 466 | 7/1962 |
| WO | WO 91/19717 | 12/1991 |
| WO | WO 96/28429 | 9/1996 |
| WO | WO 97/05138 | 2/1997 |
| WO | WO 98/28301 | 7/1998 |
| WO | WO 98/46606 | 10/1998 |
| WO | WO 98/52568 | 11/1998 |
| WO | WO 01/27113 | 4/2001 |
| WO | WO 02/074312 | 9/2002 |
| WO | WO 03/002567 | 1/2003 |
| WO | WO 03/020702 | 3/2003 |
| WO | WO 03/037899 | 5/2003 |
| WO | WO 2004/018474 | 3/2004 |
| WO | WO 2004/056831 | 7/2004 |
| WO | WO 2004/087906 | 10/2004 |
| WO | WO 2006/133261 | 12/2006 |
| WO | WO 2007/025103 | 3/2007 |
| WO | WO 2007/031977 | 3/2007 |
| WO | WO 2007/143568 | 12/2007 |
| WO | WO 2008/063505 | 5/2008 |
| WO | WO 2009/022007 | 2/2009 |
| WO | WO 2009/073210 | 6/2009 |
| WO | WO 2009/075784 | 6/2009 |
| WO | WO 2009/131974 | 10/2009 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/171016 | 12/2012 |

OTHER PUBLICATIONS

Bender et al; "Cyclic Nucleotide Phosphodiesterases: Molecular Regulation to Clinical Use", Pharmcol. Rev., 2006, 58, pp. 488-520.

Fienberg et al; "DARPP-32: Regulator of the Efficacy of Dopaminergic Neurotransmission", Science, (1998) 281, pp. 838-842.

Gilbert, A., et al., "Pyrazolopyrimidine-2,4-dione Sulfonamides: Novel and Selective Calcitonin Inducers," J. Med. Chem., (2002), 45: pp. 2342-2345.

Greengard, P. et al., "Beyond the Dopamine Receptor: the DARPP-32/Protein Phosphatase-1 Cascade", Neuron, 1999, 23, pp. 435, 447.

Lundqvist et al, Nature (2007) 447:817-822.

Mani, S.K. et al., "Requirement for DARPP-32 in Progesterone-Facilitated Sexual Receptivity in Female Rats and Mice", Science, 2000, 287, pp. 1053-1056.

Murray, F. et al., "Expression and activity of cAMP phosphodiesterase isoforms in pulmonary artery smooth muscle cells from patients with pulmonary hypertension: role for PDE1", Am. J. Physiol. Lung Cell Mol. Physiol., 2007, 292, pp. L294-L303.

Nishi et al, J Neurosci (1997) 17:8147-8155.

Poulsen et al, Bioorg & Med Chem Letter (2001) 11:191-193.

Reed, T.M. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning", The Journal of Neuroscience, 2002, 22(12), pp. 5188-5197.

Rybalkin, S.D. et al., "Cyclic GMP Phosphodiesterases and Regulation of Smooth Muscle Function", Circ. Res., 2003, 93, pp. 280-291.

Turko et al, Mol Pharmacol (1990) 56:124-130.

Xia, Y. et al., Synthesis and Evaluation of Polycyclic Pyrazolo[34-d]pyrimidines as PDE1 and PDE5 cGMP Phosphodiesterase Inhibitors, Journal Medicinal Chemistry, 1997, 40, pp. 4372-4377.

Al-Afaleq, E., et al., "Heterocyclic o-Aminonitriles: Preparation of Pyrazolo[3,4-d]-pyrimidines with Modification of the substituents at the 1-position", Molecules, 6, pp. 621-638, (2001).

Gelbin, et al., "Ketene-S, N-acetals as synthons for heterocycles new synthesis of pyrimidinones", Journal Fuer Praktische Chemie, vol. 329, No. 5, pp. 753-766, (1987).

Goodman & Gilman, The Pharmacological Basis of Therapeutics, McGraw-Hill Interamericana. 2007, p. 892.

Noguchi, M., et al., "A Facile Preparation of 7-(Substituted amino)-6 H-pyrrolo[3,7-d]-pyrimidine Derivativesl)", Bulletin of The Chemical Society of Japan, vol. 62, pp. 3043-3045, (Jan. 1, 1989).

Park, et al., "Traumatic Brain Injury: Can the consequences be stopped?" CMAJ, 178(9), 1163-1170, (2008).

Wermuth, CG, ed., "Molecular Variations based on isosteric replacements" The Practice of Chemistry, Technomics, Inc., vol. 1, Section 13, pp. 235-271 (Aug. 15, 1998) Japanese Translated Version.

* cited by examiner

PYRAZOLO[3,4-D]PYRIMIDINE-4,6(5H,7H)-DIONES AS PHOSPHODIESTERASE 1 INHIBITORS

CROSS REFERENCE TO RELATED APPLICATIONS

This application is a 35 U.S.C. §371 National Phase Application of International Application No. PCT/US2007/070551, filed Jun. 6, 2007, claiming priority to U.S. Provisional Application Nos. 60/811,687, filed Jun. 6, 2006, and 60/873,185, filed Dec. 5, 2006, the contents of each of which are incorporated herein by reference in their entirety.

STATEMENT REGARDING GOVERNMENT FUNDING

This invention was made, in part, with government support under Grant. No. 2R44MH067488 awarded by NIMH and Grant No. DAMD-17-03-1-0396 awarded by USAMRMC. The government has certain rights in the invention.

TECHNICAL FIELD

The present invention relates to novel 2-(optionally hetero)arylmethyl-3-(optionally hetero)arylamino-[2H]-pyrazolo[3,4-d]pyrimidine-4,6(5H,7H)-dione compounds, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as Parkinson's disease, depression, narcolepsy and damage to cognitive function, e.g., in schizophrenia or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

There is thus a need for compounds that selectively inhibit PDE1 activity, especially PDE1B activity.

SUMMARY OF THE INVENTION

The invention provides novel 2-(optionally hetero)arylmethyl-3-(optionally hetero)arylamino-[2H]-pyrazolo[3,4-d]pyrimidine-4,6(5H,7H)-diones, in free, salt or prodrug form (hereinafter "Compounds of the Invention"). The (optionally) hetero aryl moiety at the 2-position is preferably benzyl or pyridyl methyl para-substituted relative to the point of attachment with aryl or heteroaryl, e.g., substituted with phenyl, pyridyl or thiadiazolyl. These compounds are surprisingly found to selectively inhibit phosphodiesterase 1 (PDE1) activity, e.g., PDE1A, PDE1B, and PDE1C activity, especially PDE1B activity.

Preferably, the Compounds of the Invention are pyrazolo[3,4-d]pyrimidine-4,6(5H,7H)-diones of formula I

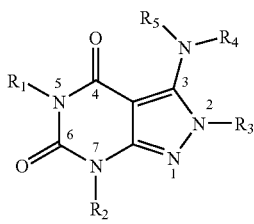

Formula I wherein
(i) $R_1$ is H or alkyl (e.g., methyl);
(ii) $R_2$ is H, alkyl (e.g., isobutyl, 2-methylbutyl, 2,2-dimethyl propyl), cycloalkyl (e.g., cyclopentyl, cyclohexyl), haloalkyl (e.g., trifluoromethyl, 2,2,2-trifluoroethyl), alkylaminoalkyl (e.g., 2-(dimethylamino)ethyl), hydroxyalkyl (e.g., 3-hydroxy-2-methyl propyl), arylalkyl (e.g., benzyl), heteroarylalkyl (e.g., pyridylmethyl), or alkoxyarylalkyl (e.g., 4-methoxybenzyl);
(iii) $R_3$ is a substituted heteroarylaklyl, e.g., substituted with haloalkyl
or
$R_3$ is attached to one of the nitrogens on the pyrazolo portion of Formula I and is a moiety of Formula A

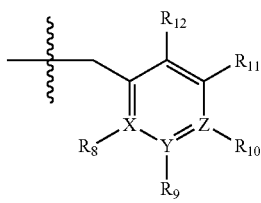

Formula A wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;
(iv) $R_4$ is aryl (e.g., phenyl) or heteroaryl; and
(v) $R_5$ is H, alkyl, cycloalkyl (e.g., cyclopentyl), heteroaryl, aryl, p-benzylaryl (e.g., biphenyl-4-ylmethyl);
wherein "alk" or "alkyl" refers to $C_{1-6}$ alkyl and "cycloalkyl" refers to $C_{3-6}$ cycloalkyl; in free, salt or prodrug form.

The invention further provides compounds of Formula I as follows:
1.1 Formula I wherein $R_1$ is methyl;
1.2 Formula I or 1.1 wherein $R_2$ is $C_{1-6}$ alkyl;
1.3 Formula 1.2 wherein $R_2$ is isobutyl, 2,2-dimethyl propyl, or 2-methylbutyl;
1.4 Formula I or 1.1 wherein $R_2$ is hydroxy $C_{1-6}$ alkyl;
1.5 Formula I or 1.1 wherein $R_2$ is 3-hydroxy-2-methyl propyl;
1.6 Formula I or 1.1 wherein $R_2$ is $C_{1-6}$ alkoxy-benzyl;
1.7 Formula 1.6 wherein $R_2$ is p-methoxybenzyl;
1.8 Formula I or 1.1 wherein $R_2$ is $C_{3-6}$ cycloalkyl;
1.9 Formula 1.8 wherein $R_2$ is cyclopentyl or cyclohexyl;
1.10 Formula I or 1.1 wherein $R_2$ is $C_{1-6}$ haloalkyl;
1.11 Formula 1.10 wherein $R_2$ is 2,2,2-trifluoroethyl;
1.12 Any of the preceding formulae wherein $R_3$ is a moiety of Formula A wherein $R_8$, $R_9$, $R_{11}$ and $R_{12}$ are each H and $R_{10}$ is phenyl;
1.13 Any of the preceding formulae I-1.11 wherein $R_3$ is a moiety of Formula A wherein $R_8$, $R_9$, $R_{11}$ and $R_{12}$ are each H and $R_{10}$ is pyridyl or thiadizolyl;
1.14 Formula 1.13 wherein $R_3$ is a moiety of Formula A wherein $R_8$, $R_9$, $R_{11}$ and $R_{12}$ are each H and $R_{10}$ is 2-pyridyl;
1.15 Any of the preceding formulae wherein $R_4$ is phenyl;
1.16 Any of the preceding formulae wherein $R_5$ is H,
1.17 Any of the preceding formulae wherein X, Y and Z are all C;
1.18 Any of the preceding formulae wherein $R_2$ is tetrahydrofuran-2-ylmethyl;
1.19 Any of the preceding formulae wherein $R_{10}$ is pyrimidinyl;
1.20 A compound of formula 1.19 wherein the pyrimidinyl is 5-fluoropyrmidinyl;
1.21 Any of the preceding formulae wherein $R_{10}$ is pyrazol-1-yl;
1.22 Any of the preceding formulae wherein $R_{10}$ is 1,2,4-triazol-1-yl;
1.23 Any of the preceding formulae wherein $R_{10}$ is aminocarbonyl;
1.24 Any of the preceding formulae wherein $R_{10}$ is methylsulfonyl;
1.25 Any of the preceding formulae wherein $R_{10}$ is 5-methyl-1,2,4-oxadiazol-3-yl;
1.26 Any of the preceding formulae wherein $R_{10}$ is 5-fluoropyrimidin-2-yl;
1.26 Any of the preceding formulae wherein $R_4$ is 4-fluorophenyl;
1.27 Any of the preceding formulae wherein $R_{10}$ is trifluoromethyl;
1.28 Any of the preceding formulae wherein $R_3$ is a moiety of Formula A, X and Z are C, and Y is N;
1.29 A compound selected from the compounds of Examples 1-24 below; and/or
1.30 Any one of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 25;
such compounds according to any of the preceding formulae being in free, salt or prodrug form.

In an especially preferred embodiment, the Compounds of the Invention are compounds of Formula I wherein
(i) $R_1$ is methyl;
(ii) $R_2$ is $C_{1-6}$ alkyl;
(iii) $R_3$ is a moiety of Formula A wherein X, Y and Z are all C and $R_8$, $R_9$, $R_{11}$ and $R_{12}$ are each H and $R_{10}$ is phenyl, pyridyl (for example, pyrid-2-yl), or thiadiazolyl (e.g., 1,2,3-thiadiazol-4-yl);

(iv) $R_4$ is phenyl; and
(v) $R_5$ is H;
in free or salt form.

For example, preferred Compounds of the Invention include compounds according to Formula II

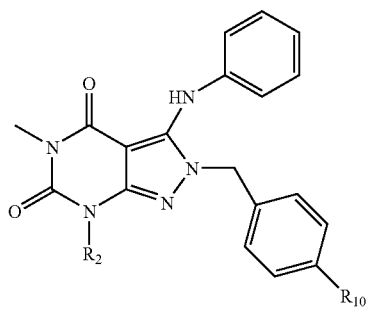

Formula II wherein
$R_2$ is H, alkyl (e.g., isobutyl, 2-methylbutyl, 2,2-dimethyl propyl), cycloalkyl (e.g., cyclopentyl, cyclohexyl), heteroaryl (e.g., pyridyl), aryl (e.g., phenyl), haloalkyl (e.g., trifluoromethyl, 2,2,2-trifluoroethyl), alkylaminoalkyl (e.g., 2-(dimethylamino)ethyl), hydroxyalkyl (e.g., 3-hydroxy-2-methyl propyl), arylalkyl (e.g., benzyl), or alkoxyarylalkyl (e.g., 4-methoxybenzyl);
wherein "alk" or "alkyl" refers to $C_{1-6}$ alkyl; and
$R_{10}$ is phenyl, pyridyl (for example, pyrid-2-yl) or thiadiazolyl (for example, 1,2,3-thiadiazol-4-yl);
in free, salt or prodrug form.

In certain embodiments, the Compounds of the Invention are compounds of Formula II wherein
$R_2$ is H, alkyl (e.g., isobutyl, 2-methylbutyl, 2,2-dimethyl propyl), cycloalkyl (e.g., cyclopentyl, cyclohexyl, tetrahydrofuran-2-ylmethyl), heteroaryl (e.g., pyridyl), aryl (e.g., phenyl), haloalkyl (e.g., trifluoromethyl, 2,2,2-trifluoroethyl), alkylaminoalkyl (e.g., 2-(dimethylamino)ethyl), hydroxyalkyl (e.g., 3-hydroxy-2-methyl propyl), arylalkyl (e.g., benzyl), or alkoxyarylalkyl (e.g., 4-methoxybenzyl);
and
$R_{10}$ is phenyl, pyridyl (for example, pyrid-2-yl), pyrimidinyl (e.g., 5-fluoropyrimidin-2-yl), pyrazolyl (e.g. pyrazol-1-yl), thiadiazolyl (for example, 1,2,3-thiadiazol-4-yl), haloalkyl (e.g., trifluoromethyl), alkylsulfonyl (e.g., methylsulfonyl), oxadiazolyl (e.g., 5-methyl-1,2,4-oxadiazol-3-yl), aminocarbonyl (e.g., so as to form a 4-benzamide structure), triazolyl (e.g., 1,2,4-triazol-1-yl);
wherein "alk" or "alkyl" refers to $C_{1-6}$ alkyl;
in free, salt or prodrug form.

If not otherwise specified or clear from context, the following terms herein have the following meanings:
(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.
(b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. In certain embodiments, the cycloalkyl may optionally contain one or more heteroatoms e.g., nitrogen, oxygen or sulfur, in the ring or linking portion of the moiety, e.g., tetrahydrofuranylmethyl
(c) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).
(d) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.
(e) For ease of reference, the atoms on the pyrazolo-pyrimidine core of the Compounds of the Invention are numbered in accordance with the numbering depicted in Formula 1, unless otherwise noted.

Compounds of the Invention may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. As will be appreciated the term thus embraces conventional pharmaceutical prodrug forms.

The invention also provides methods of making the Compounds of the Invention, novel intermediates useful for making Compounds of the Invention, and methods of using the Compounds of the Invention for treatment of diseases and disorders as set forth below (especially treatment of diseases characterized by reduced dopamine D1 receptor signaling activity, such as Parkinson's disease, Tourette's Syndrome, Autism, fragile X syndrome, ADHD, restless leg syndrome, depression, and cognitive impairment of schizophrenia).

DETAILED DESCRIPTION OF THE INVENTION

Methods of Making Compounds of the Invention

The compounds of the formula I and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. All references cited herein are hereby incorporated in their entirety by reference.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks. Solvent mixture compositions are given as volume percentages or volume ratios. In cases where the NMR spectra are complex, only diagnostic signals are reported.

TERMS AND ABBREVIATIONS

Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
K$_2$CO$_3$=potassium carbonate,
MeOH=methanol,
NaHCO$_3$=sodium bicarbonate,
NH$_4$OH=ammonium hydroxide,
PMB=p-methoxybenzyl,
POCl$_3$=phosphorous oxychloride,
SOCl$_2$=thionyl chloride,
TFA=trifluoroacetic acid,
THF=tetrahedrofuran.

The synthetic methods in this invention are illustrated below. The significances for the R groups are as set forth above for formula I unless otherwise indicated.

In an aspect of the invention, intermediate compounds of formula IIb can be synthesized by reacting a compound of formula IIa with a dicarboxylic acid, acetic anhydride and acetic acid mixing with heat for about 3 hours and then cooled:

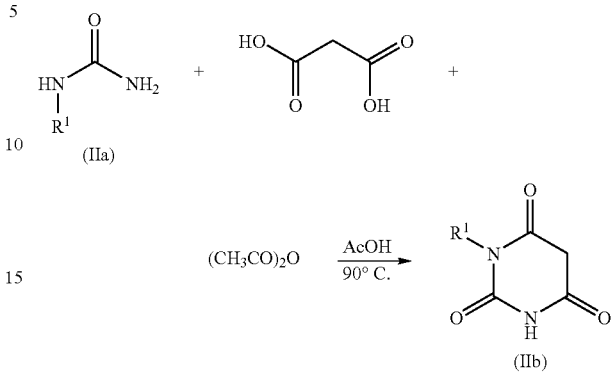

wherein R$^1$ is H or C$_{1-4}$alkyl [e.g., methyl].

Intermediate IIc can be prepared by for example reacting a compound of IIb with for example a chlorinating compound such as POCl$_3$, sometimes with small amounts of water and heated for about 4 hours and then cooled:

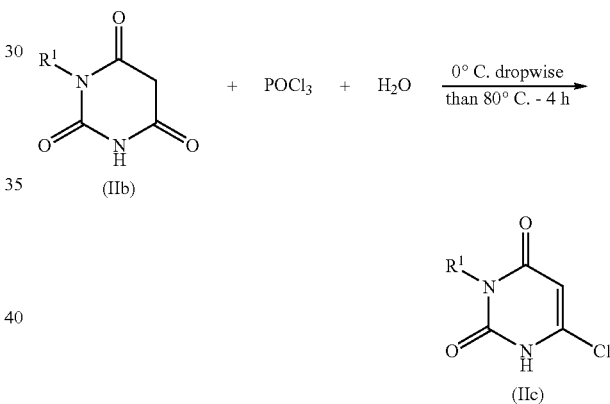

Intermediate IId may be formed by reacting a compound of IIc with for example a P$^1$—X in a solvent such as DMF and a base such as K$_2$CO$_3$ at room temperature or with heating:

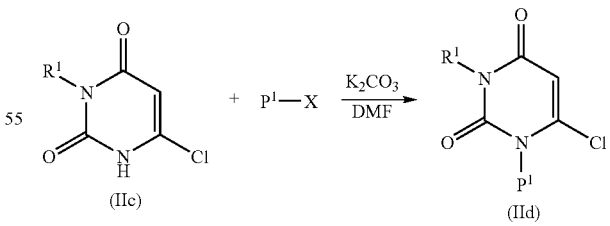

wherein P$^1$ is a protective group [e.g., p-methoxybenzyl group (PMB)]; X is a leaving group such as a halogen, mesylate, or tosylate.

Intermediate IIe may be prepared by reacting a compound of IId with hydrazine or hydrazine hydrate in a solvent such as methanol and refluxed for about 4 hours and then cooled:

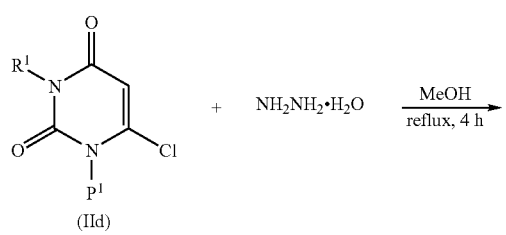

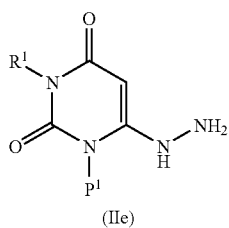

Intermediate IIf can be synthesized by reacting a compound of IIe with for example an aryl isothiocyanate or isocyanate in a solvent such as DMF and heated at 110° C. for about 2 days and then cooled:

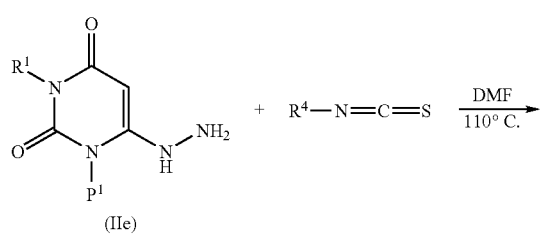

wherein $R^4$ is (hetero)aryl or (hetero)arylmethyl [e.g., phenyl or benzyl].

Intermediate IIg may be formed by reacting a compound of IIf with for example a $R^3$—X in a solvent such as DMF and a base such as $K_2CO_3$ at room temperature or with heating:

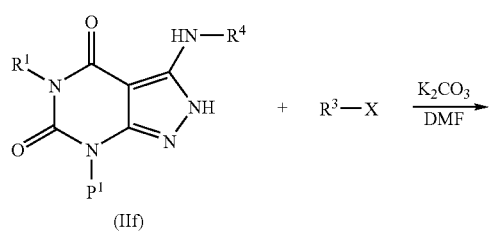

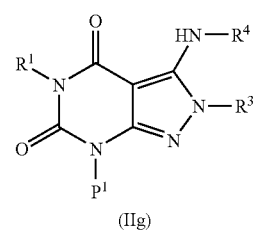

wherein $R^3$ is as defined previously [e.g. an optionally substituted benzyl group]; X is a leaving group such as a halogen, mesylate, or tosylate.

Intermediate IIh may be synthesized from a compound of IIg by removing the protective group $P^1$ with an appropriate method. For example, if $P^1$ is a p-methoxybenzyl group, then it can be removed with $AlCl_3$ in the presence of anisole at room temperature:

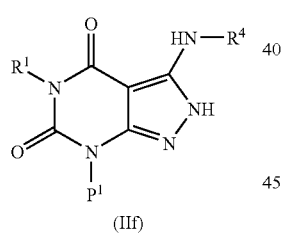

Compound I may be formed by reacting a compound of IIh with for example a $R^2$—X and/or $R^5$—X in a solvent such as DMF and a base such as $K_2CO_3$ at room temperature or with heating:

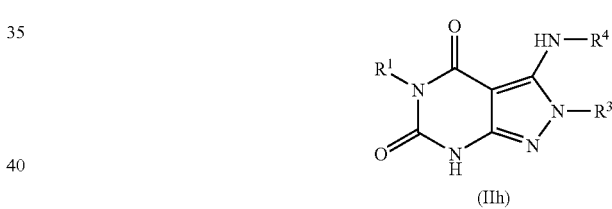

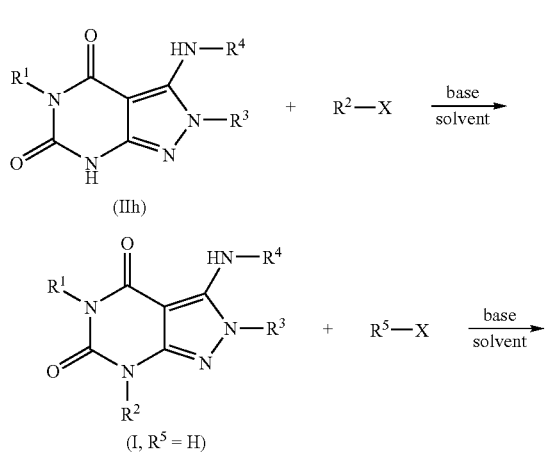

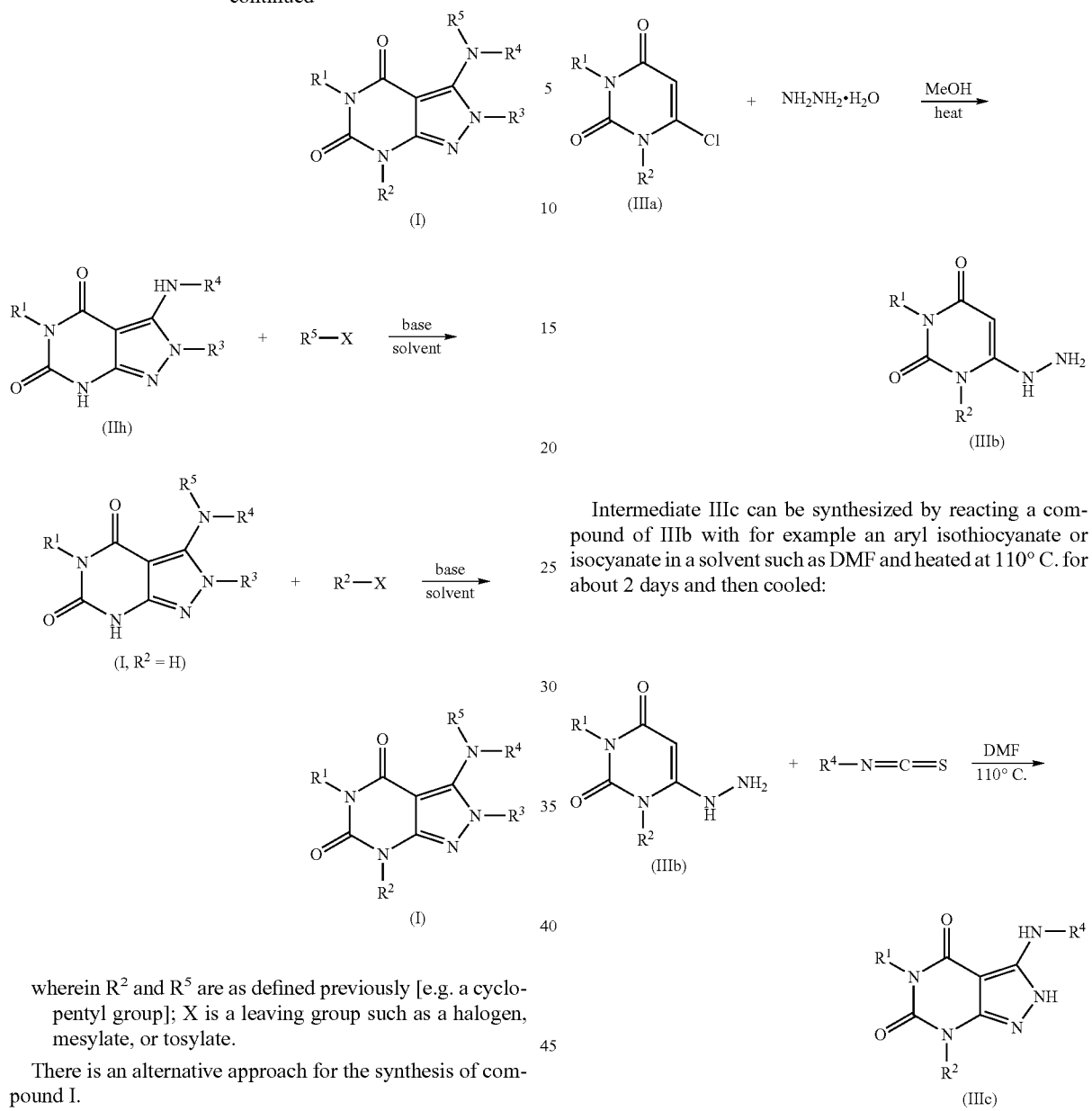

wherein $R^2$ and $R^5$ are as defined previously [e.g. a cyclopentyl group]; X is a leaving group such as a halogen, mesylate, or tosylate.

There is an alternative approach for the synthesis of compound I.

Intermediate IIIa may be formed by reacting a compound of IIc with for example a $R^2$—X in a solvent such as DMF and a base such as $K_2CO_3$ at room temperature or with heating:

Intermediate IIIb may be prepared by reacting a compound of IIIa with hydrazine or hydrazine hydrate in a solvent such as methanol and heated for about several hours and then cooled:

Intermediate IIIc can be synthesized by reacting a compound of IIIb with for example an aryl isothiocyanate or isocyanate in a solvent such as DMF and heated at 110° C. for about 2 days and then cooled:

Compound I may be formed by reacting a compound of IIIc with for example a $R^3$—X in a solvent such as DMF and a base such as $K_2CO_3$ at room temperature or with heating. The obtained product I ($R^5$═H) may further react with for example a $R^5$—X under basic condition to give compound I:

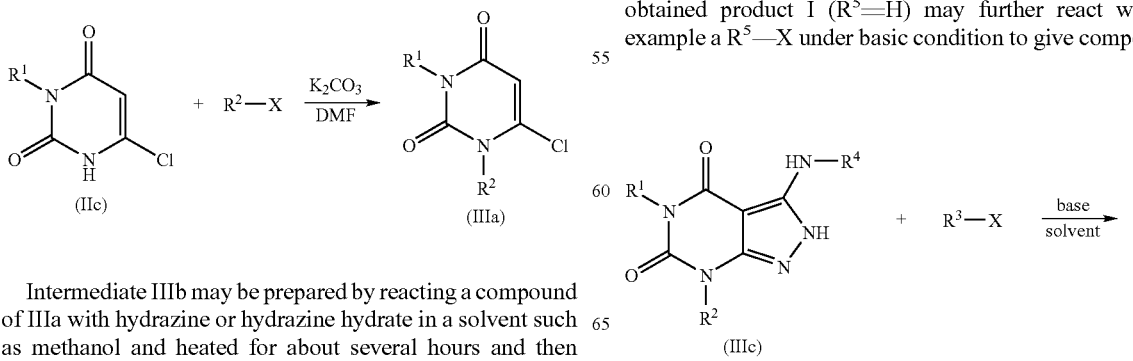

-continued

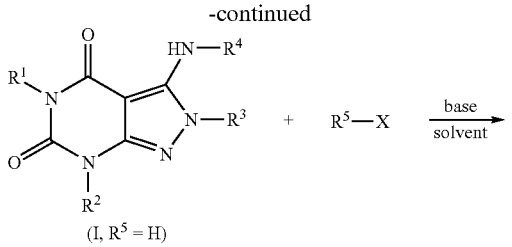

(I, R⁵ = H)

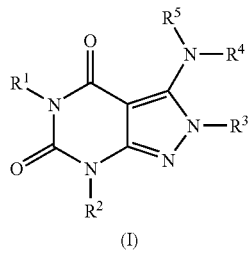

(I)

The invention thus provides methods of making Compounds of the Invention as described above, for example, comprising (i) reacting a 2H-pyrazolo[3,4-d]pyrimidine-4,6(5H,7H)-dione with a compound of formula X—R³ wherein X is a leaving group, e.g., halogen, mesylate, or tosylate, and R³ is optionally substituted arylalkyl or heteroarylalkyl, for example wherein R³ is a substituted benzyl of formula A as defined above, e.g., under basic conditions, for example wherein the 2H-pyrazolo[3,4-d]pyrimidine-4,6(5H,7H)-dione is a compound of Formula IIc:

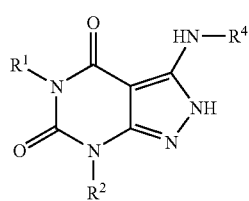

(IIIc)

wherein $R_1$, $R_2$ and $R_4$ are as defined above, e.g., with reference to Formula I; and/or (ii) reacting a 2H-pyrazolo[3,4-d]pyrimidine-4,6(5H,7H)-dione with a compound of formula X—R² wherein X is a leaving group, e.g., halogen, mesylate, or tosylate, and R² is alkyl, cycloalkyl, arylalkyl or heterocycloalkyl, for example wherein R² is isobutyl; e.g., under basic conditions, for example wherein the 2H-pyrazolo[3,4-d]pyrimidine-4,6(5H,7H)-dione is a compound of Formula IIh:

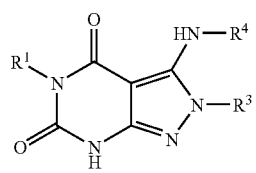

(IIh)

wherein $R_1$, $R_3$ and $R_4$ are as defined above, e.g., with reference to Formula I.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:

(i) Neurodegenerative diseases, including Parkinson's disease, restless leg, tremors, dyskinesias, Huntington's disease, Alzheimer's disease, and drug-induced movement disorders;

(ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;

(iii) Circulatory and cardiovascular disorders, including cerebrovascular disease, stroke, congestive heart disease, hypertension, pulmonary hypertension, and sexual dysfunction;

(iv) Respiratory and inflammatory disorders, including asthma, chronic obstructive pulmonary disease, and allergic rhinitis, as well as autoimmune and inflammatory diseases;

(v) Any disease or condition characterized by low levels of cAMP and/or cGMP (or inhibition of cAMP and/or cGMP signaling pathways) in cells expressing PDE1; and/or (vi) Any disease or condition characterized by reduced dopamine D1 receptor signaling activity, comprising administering an effective amount of a Compound of the Invention, e.g., a compound according to any of Formula 1-1.30 or Formula II, to a human or animal patient in need thereof.

In an especially preferred embodiment, the invention provides methods of treatment or prophylaxis for narcolepsy. In this embodiment, PDE 1 Inhibitors may be used as a sole therapeutic agent, but may also be used in combination or for co-administration with other active agents. Thus, the invention further comprises a method of treating narcolepsy comprising administering simultaneously, sequentially, or contemporaneously administering therapeutically effective amounts of (i) a PDE 1 Inhibitor, e.g., a compound according to any of Formula 1-1.30 or Formula II, and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB).

to a human or animal patient in need thereof.

In another embodiment, the invention further provides methods of treatment or prophylaxis of a condition which may be alleviated by the enhancement of the progesterone signaling comprising administering an effective amount of a Compound of the Invention, e.g., a compound according to any of Formula 1-1.30 or Formula II, to a human or animal patient in need thereof. Disease or condition that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmmune disease, multiple sclerosis, prostate enlargement, prostate cancer, and hypothyroidism. For example, by enhancing progesterone signaling, the PDE 1 inhibitors may be used to encourage egg implantation through effects on the lining of uterus, and to help maintain pregnancy in women who are prone to miscarriage due to immune response to pregnancy or low progesterone function. The novel PDE 1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE 1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of (i) a PDE 1 Inhibitor, e.g., a compound according to any of Formula 1-1.30 or Formula II, and (ii) a hormone, e.g., selected from estrogen and estrogen analogues (e.g., estradiol, estriol, estradiol esters) and progesterone and progesterone analogues (e.g., progestins)

to a human or animal patient in need thereof.

The invention also provides a method for enhancing or potentiating dopamine D1 intracellular signaling activity in a cell or tissue comprising contacting said cell or tissue with an amount of a Compound of the Invention sufficient to inhibit PDE1B activity.

The invention also provides a method for enhancing or potentiating progesterone signaling activity in a cell or tissue comprising contacting said cell or tissue with an amount of a Compound of the Invention sufficient to inhibit PDE1B activity.

The invention also provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention that inhibits PDE1B, wherein PDE1B activity modulates phosphorylation of DARPP-32 and/or the GluR1 AMPA receptor.

The present invention also provides (i) a Compound of the Invention for use as a pharmaceutical, for example for use in any method or in the treatment of any disease or condition as hereinbefore set forth, (ii) the use of a Compound of the Invention in the manufacture of a medicament for treating any disease or condition as hereinbefore set forth, (iii) a pharmaceutical composition comprising a Compound of the Invention in combination or association with a pharmaceutically acceptable diluent or carrier, and (iv) a pharmaceutical composition comprising a Compound of the Invention in combination or association with a pharmaceutically acceptable diluent or carrier for use in the treatment of any disease or condition as hereinbefore set forth.

The words "treatment" and "treating" are to be understood accordingly as embracing prophylaxis and treatment or amelioration of symptoms of disease as well as treatment of the cause of the disease.

Compounds of the Invention are in particular useful for the treatment of Parkinson's disease, narcolepsy and female sexual dysfunction.

Compounds of the Invention may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE 1 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1

2-(Biphenyl-4-ylmethyl)-7-isobutyl-5-methyl-3-(phenylamino)-2H-pyrazolo[3,4-d]pyrimidine-4,6(5H,7H)-dione

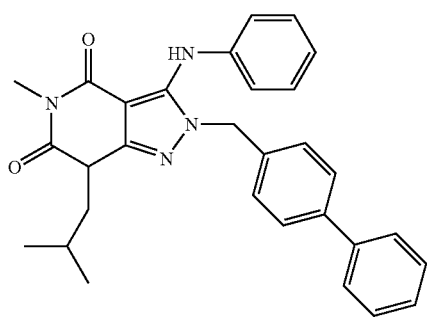 [SMILES: CC(C)CC1C(=O)N(C)C(=O)c2c1nn(Cc1ccc(-c3ccccc3)cc1)c2Nc1ccccc1]

(a) 1-Methylpyrimidine-2,4,6(1H,3H,5H)-trione

To a solution of malonic acid (80 g, 0.79 mol) and methylurea (50 g, 0.68 mol) in 180 ml of acetic acid at 70° C., acetic anhydride (130 ml, 1.37 mol) is added slowly. After the completion of the addition, the reaction mixture is stirred at 90° C. for 3 hours, and then cooled to room temperature. The solvent is removed under reduced pressure, and the residue is treated with 350 mL of ethanol to precipitate out yellowish solid. The solid is recrystallized from ethanol to give 63.1 g product as crystalline solids (Yield: 65.8%). m.p.=131.2-133.1° C. [Lit.[1]: m.p.=130-131.5° C.].

(b) 6-Chloro-3-methylpyrimidine-2,4(1H,3H)-dione

Water (2.7 mL) is added dropwise to a suspension of 1-methylpyrimidine-2,4,6(1H,3H,5H)-trione (14.2 g, 100 mol) in $POCl_3$ (95 mL) at 0° C. The reaction mixture is then heated at 80° C. for 5 hours. The resulting brownish solution is cooled, and $POCl_3$ is evaporated under reduced pressure. The residue is treated with MeOH, and the obtained solid is recrystallized from ethanol to give 11.5 g product (Yield: 71.6%). m.p.=279-282° C. (dec) [Lit.[2]: 280-282° C.]. $^1$H NMR (400 MHz, DMSO-$d_6$) δ3.10 (S, 3H), 5.90 (S, 1H), 12.4 (br, 1H).

(c) 6-Chloro-1-isobutyl-3-methylpyrimidine-2,4(1H,3H)-dione

A mixture of 6-chloro-3-methylpyrimidine-2,4(1H,3H)-dione (3 g, 18.8 mmol), isobutyl iodide (5 mL, 43.5 mmol) and potassium carbonate (5.3 g, 38.4 mmol) in anhydrous DMF (200 mL) is heated at 50° C. for 8 hours. Additional isobutyl iodide (4.3 mL, 37.5 mmol) is added, and the reaction mixture heated at 50° C. for 24 hours. After hot filtration, the filtrate is evaporated to dryness under reduced pressure. The obtained oil is further purified by silica-gel flash chromatography to give 2.1 g of pure product (Yield: 52%).

(d) 6-Hydrazinyl-1-isobutyl-3-methylpyrimidine-2,4(1H,3H)-dione

To a solution of 6-chloro-1-isobutyl-3-methylpyrimidine-2,4(1H,3H)-dione (2.0 g 9.3 mmol) in EtOH (8 mL), hydrazine monohydrate (1.3 mL) in EtOH (3 mL) is added slowly. The reaction mixture is refluxed for 5 hours, and then cooled. A large amount of AcOEt is added into the reaction mixture, and then cooled and filtered to give 1.95 g of product as yellowish solids (Yield: 100%).

(e) 7-Isobutyl-5-methyl-3-(phenylamino)-2H-pyrazolo[3,4-d]pyrimidine-4,6(5H,7H)-dione Phenyl isothiocyanate (0.17 mL, 1.4 mmol) is added to a solution of 6-hydrazinyl-1-isobutyl-3-methylpyrimidine-2,4(1H,3H)-dione (31 mg, 0.47 mmol) in DMF (10 mL). The reaction mixture is heated at 120° C. for 6 hours, and then evaporated to remove solvent under reduced pressure. The residue is further purified by silica-gel flash chromatography to give 20 mg of product (Yield: 41%). $^1$H NMR (400 MHz, DMSO-$d_6$) δ0.95 (s, 3H), 0.97 (s, 3H), 2.30 (m, 1H), 3.37 (s, 3H), 3.77 (d, 2H), 7.16-7.43 (m, 5H), 7.61 (s, 1H). MS (FAB) m/z 314.3 $[M+H]^+$.

(f) 2-(Biphenyl-4-ylmethyl)-7-isobutyl-5-methyl-3-(phenylamino)-2H-pyrazolo[3,4-d]pyrimidine-4,6(5H,7H)-dione A mixture of 7-isobutyl-5-methyl-1H-pyrazolo[3,4-d]pyrimidine-4,6(5H,7H)-dione (12.0 g, 0.0383 mmol), p-biphenylmethyl bromide (9.46 mg, 0.0383 mmol) and potassium carbonate (5.3 mg, 0.0383 mmol) in acetone (2.5 mL) is stirred at room temperature overnight. The solvent is evaporated under reduced pressure. The residue is directly purified by chromatography to give 7.0 mg product as white solids (Yield: 38.0%). $^1$H NMR (400 MHz, CDCl$_3$) δ0.97 (s, 3H), 0.99 (s, 3H), 2.33 (m, 1H). 3.34 (s, 3H), 3.85 (d, 2H), 4.99 (s, 2H), 6.76 (s, 1H), 6.91-7.56 (m, 13H). MS (FAB) m/z 480.3 $[M+H]^+$.

Example 2

2-(Biphenyl-4-ylmethyl)-7-(4-methoxybenzyl)-5-methyl-3-(phenylamino)-2H-pyrazolo[3,4-d]pyrimidine-4,6(5H,7H)-dione

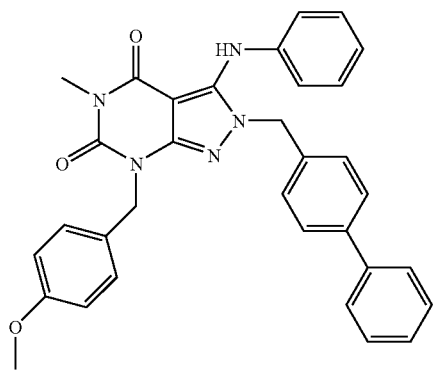 [SMILES: COc1ccc(Cn2c(=O)n(C)c(=O)c3c(Nc4ccccc4)n(Cc4ccc(-c5ccccc5)cc4)nc32)cc1]

The synthesis method is analogous to example 1 wherein p-methoxybenzyl chloride is added in step (c) instead of isobutyl iodide. TLC $R_f$=0.61 (AcOEt:Hexanes=1:1). $^1$H NMR (CDCl$_3$) δ3.31 (s, 3H), 3.71 (s, 3H), 4.99 (s, 2H), 5.10 (s, 2H), 6.75-7.57 (m, 19H). MS (FAB) m/z 544.4 [M+H]$^+$ Example 3

2-(Biphenyl-4-ylmethyl)-3-((biphenyl-4-ylmethyl)(phenyl)amino)-7-(4-methoxybenzyl)-5-methyl-2H-pyrazolo[3,4-d]pyrimidine-4,6(5H,7H)-dione

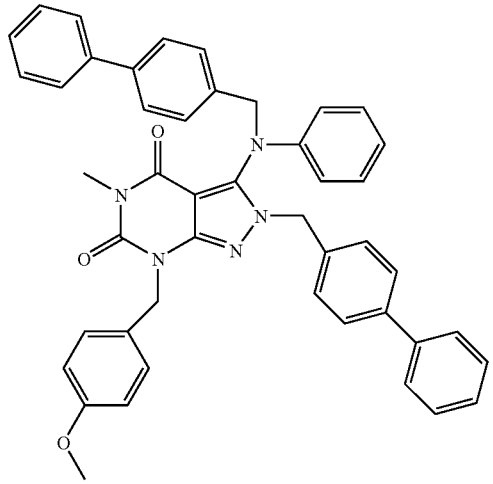 [SMILES: COc1ccc(Cn2c(=O)n(C)c(=O)c3c(N(Cc4ccc(-c5ccccc5)cc4)c4ccccc4)n(Cc4ccc(-c5ccccc5)cc4)nc32)cc1]

The synthesis method is analogous to example 1 wherein p-methoxybenzyl chloride is added in step (c) instead of isobutyl iodide. TLC R$_f$=0.81 (AcOEt:Hexanes=1:1). $^1$H NMR (CDCl$_3$) δ3.38 (s, 3H), 3.68 (s, 3H), 4.99 (s, 2H), 5.10 (s, 2H), 5.20 (s, 2H), 6.70-7.57 (m, 27H). MS (FAB) m/z 710.5 [M+H]$^+$ Example 4

7-(4-Methoxybenzyl)-5-methyl-3-(phenylamino)-2-(4-(trifluoromethyl)benzyl)-2H-pyrazolo[3,4-d]pyrimidine-4,6(5H,7H)-dione

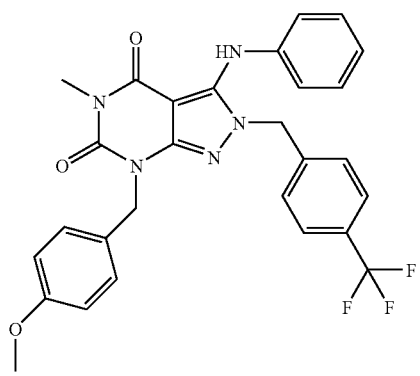 [SMILES: COc1ccc(Cn2c(=O)n(C)c(=O)c3c(Nc4ccccc4)n(Cc4ccc(C(F)(F)F)cc4)nc32)cc1]

The synthesis method is analogous to example 1 wherein p-methoxybenzyl chloride is added in step (c) instead of isobutyl iodide; and p-trifluoromethylbenzyl bromide is added in step (f) instead of p-biphenylmethyl bromide (Yield: 80%). MS (ESI) ink 536.5 [M+H]$^+$ Example 5

7-(4-Methoxybenzyl)-5-methyl-3-(phenylamino)-2-(4-(pyridin-2-yl)benzyl)-2H-pyrazolo[3,4-d]pyrimidine-4,6(5H,7H)-dione

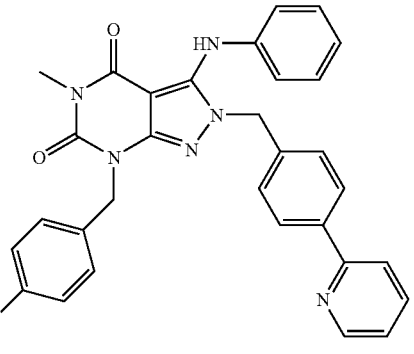

The synthesis method is analogous to example 1 wherein p-methoxybenzyl chloride is added in step (c) instead of isobutyl iodide; and p-(pyridin-2-yl)benzyl bromide is added in step (f) instead of p-biphenylmethyl bromide (Yield: 60%). MS (ESI) m/z 545.2 [M+H]$^+$ Example 6

5-Methyl-3-(phenylamino)-2-(4-(pyridin-2-yl)benzyl)-2H-pyrazolo[3,4-d]pyrimidine-4,6(5H,7H)-dione

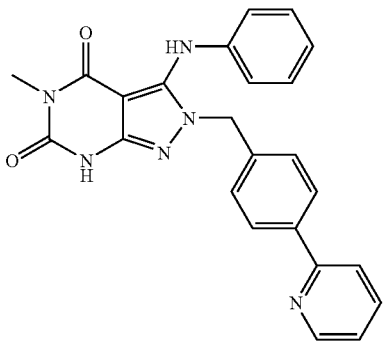 [SMILES: Cn1c(=O)[nH]c2nn(Cc3ccc(-c4ccccn4)cc3)c(Nc3ccccc3)c2c1=O]

AlCl$_3$ (0.733 g, 5.50 mmol) is added to a solution of 7-(4-methoxybenzyl)-5-methyl-3-(phenylamino)-2-(4-(pyridin-2-yl)benzyl)-2H-pyrazolo[3,4-d]pyrimidine-4,6(5H,7H)-dione (1.08 g, 1.98 mmol) and anisole (mL) in 1,2-dichloroethane (15 mL) under argon. The reaction mixture is stirred at room temperature overnight, and then quenched with water with cooling. The resulting suspension is treated with 20% NaOH (70 mL), and then extract with methylene chloride 5 times. The organic phase is combined and evapo-

Example 7

7-Cyclopentyl-5-methyl-3-(phenylamino)-2-(4-(pyridin-2-yl)benzyl)-2H-pyrazolo[3,4-d]pyrimidine-4,6(5H,7H)-dione

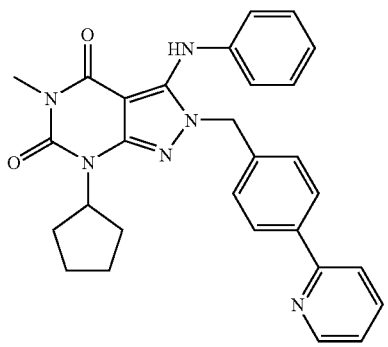 [SMILES: Cn1c(=O)c2c(Nc3ccccc3)n(Cc3ccc(-c4ccccn4)cc3)nc2n(C2CCCC2)c1=O]

Methylethylketone (1.2 mL) was added into a 0.5-5 mL reaction vessel containing 5-methyl-3-(phenylamino)-2-(4-(pyridin-2-yl)benzyl)-2H-pyrazolo[3,4-d]pyrimidine-4,6 (5H,7H)-dione (25 mg, 0.0589 mmol), iodocyclopentane (8.2 µL, 0.0707 mmol) and K$_2$CO$_3$ (9.8 mg, 0.0707 mmol). The sealed vessel was put onto a Biotage Microwave instrument and the microwave reaction was carried out at 140° C. for 1 hour. The obtained crude product was then purified by silica-gel flash chromatography to give 14.9 mg of pure product (Yield: 51.4%). TLC R$_f$=0.72 (AcOEt:Hexanes=2:1). MS (ESI) m/z 493.4 [M+H]$^+$

Example 8

3-(Cyclopentyl(phenyl)amino)-5-methyl-2-(4-(pyridin-2-yl)benzyl)-2H-pyrazolo[3,4-d]pyrimidine-4,6(5H,7H)-dione

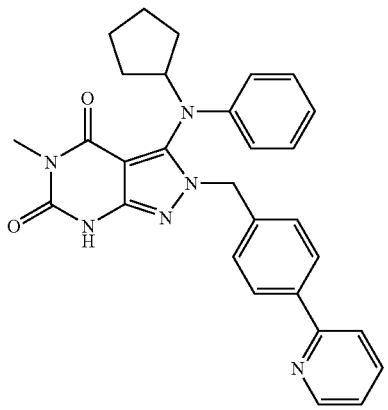 [SMILES: Cn1c(=O)[nH]c2nn(Cc3ccc(-c4ccccn4)cc3)c(N(c3ccccc3)C3CCCC3)c2c1=O]

Methylethylketone (1.2 mL) was added into a 0.5-5 mL reaction vessel containing 5-methyl-3-(phenylamino)-2-(4-(pyridin-2-yl)benzyl)-2H-pyrazolo[3,4-d]pyrimidine-4,6 (5H,7H)-dione (25 mg, 0.0589 mmol), iodocyclopentane (8.2 µL, 0.0707 mmol) and K$_2$CO$_3$ (9.8 mg, 0.0707 mmol). The sealed vessel was put onto a Biotage Microwave instrument and the microwave reaction was carried out at 140° C. for 1 hour. The obtained crude product was then purified by silica-gel flash chromatography to give 5.2 mg of pure product (Yield: 17.9%). TLC R$_f$=0.50 (AcOEt:Hexanes=2:1). MS (ESI) m/z 493.4 [M+H]$^+$

Example 9

7-Isobutyl-5-methyl-3-(phenylamino)-2-(4-(pyridin-2-yl)benzyl)-2H-pyrazolo[3,4-d]pyrimidine-4,6(5H,7H)-dione

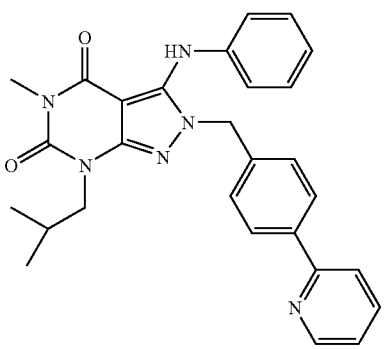 [SMILES: CC(C)Cn1c(=O)n(C)c(=O)c2c(Nc3ccccc3)n(Cc3ccc(-c4ccccn4)cc3)nc21]

The synthesis method is analogous to example 7 wherein isobutyl iodide is added instead of iodocyclopentane (Yield: 95.8%). MS (ESI) m/z 481.4 [M+H]$^+$

Example 10

7-Cyclohexyl-5-methyl-3-(phenylamino)-2-(4-(pyridin-2-yl)benzyl)-2H-pyrazolo[3,4-d]pyrimidine-4,6(5H,7H)-dione

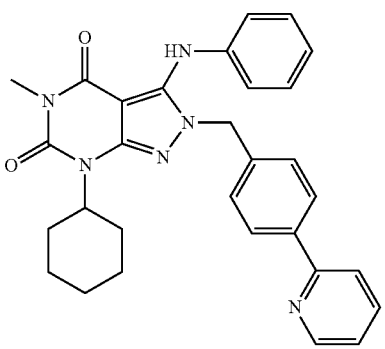 [SMILES: Cn1c(=O)c2c(Nc3ccccc3)n(Cc3ccc(-c4ccccn4)cc3)nc2n(C2CCCCC2)c1=O]

The synthesis method is analogous to example 7 wherein iodocyclohexane is added instead of iodocyclopentane (Yield: 10%). MS (ESI) m/z 507.4 [M+H]$^+$

Example 11

5-Methyl-7-neopentyl-3-(phenylamino)-2-(4-(pyridin-2-yl)benzyl)-2H-pyrazolo[3,4-d]pyrimidine-4,6(5H,7H)-dione

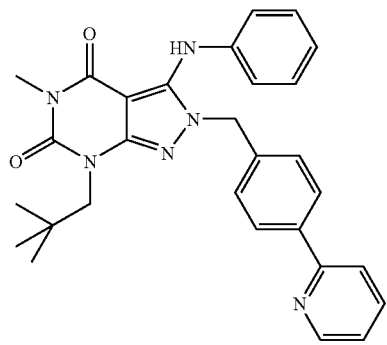 [SMILES: Cn1c(=O)c2c(Nc3ccccc3)n(Cc3ccc(-c4ccccn4)cc3)nc2n(CC(C)(C)C)c1=O]

The synthesis method is analogous to example 7 wherein 1-iodo-2,2-dimethylpropane is added instead of iodocyclopentane (Yield: 4.1%). MS (ESI) m/z 495.4 [M+H]$^+$

Example 12

1p;-.5p(S)-5-Methyl-7-(2-methylbutyl)-3-(phenylamino)-2-(4-(pyridin-2-yl)benzyl)-2H-pyrazolo[3,4-d]pyrimidine-4,6(5H,7H)-dione

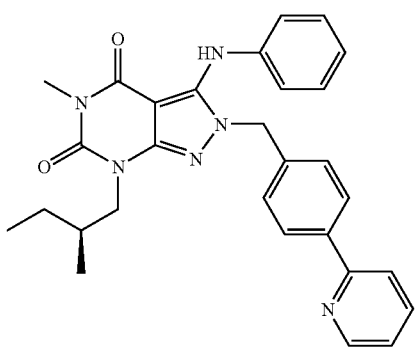 [SMILES: CC[C@H](C)Cn1c(=O)n(C)c(=O)c2c(Nc3ccccc3)n(Cc3ccc(-c4ccccn4)cc3)nc21]

The synthesis method is analogous to example 7 wherein (S)-1-iodo-2-methylbutane is added instead of iodocyclopentane (Yield: 81.8%). MS (ESI) m/z 495.4 [M+H]$^+$

Example 13

5-Methyl-3-(phenylamino)-2-(4-(pyridin-2-yl)benzyl)-7-(2,2,2-trifluoroethyl)-2H-pyrazolo[3,4-d]pyrimidine-4,6(5H,7H)-dione

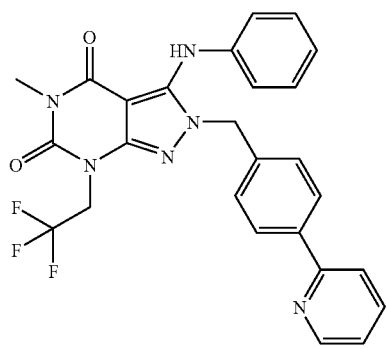 [SMILES: Cn1c(=O)c2c(Nc3ccccc3)n(Cc3ccc(-c4ccccn4)cc3)nc2n(CC(F)(F)F)c1=O]

The synthesis method is analogous to example 7 wherein 1,1,1-trifluoro-2-iodoethane is added instead of iodocyclopentane (Yield: 14.8%). MS (ESI) m/z 507.3 [M+H]$^+$

Example 14

(R)-7-(3-Hydroxy-2-methylpropyl)-5-methyl-3-(phenylamino)-2-(4-(pyridin-2-yl)benzyl)-2H-pyrazolo[3,4-d]pyrimidine-4,6(5H,7H)-dione

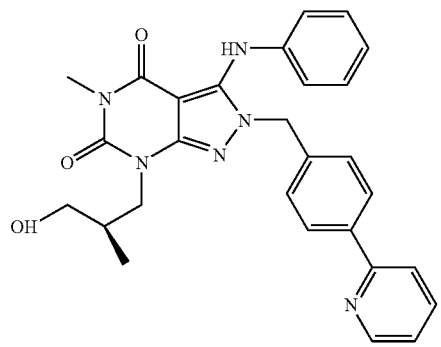 [SMILES: C[C@@H](CO)Cn1c(=O)n(C)c(=O)c2c(Nc3ccccc3)n(Cc3ccc(-c4ccccn4)cc3)nc21]

The synthesis method is analogous to example 7 wherein (S)-3-bromo-2-methylpropan-1-ol is added instead of iodocyclopentane (Yield: 86.3%). MS (ESI) m/z 497.4 [M+H]$^+$

Example 15

7-(2-(Dimethylamino)ethyl)-5-methyl-3-(phenylamino)-2-(4-(pyridin-2-yl)benzyl)-2H-pyrazolo[3,4-d]pyrimidine-4,6(5H,7H)-dione

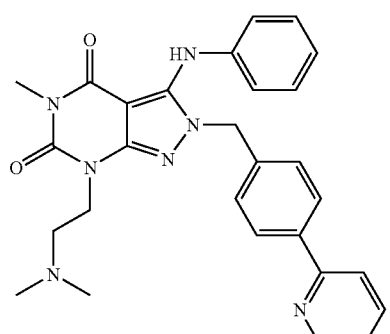

The synthesis method is analogous to example 7 wherein 2-bromo-N,N-dimethylethanaminium bromide is added instead of iodocyclopentane (Yield: 64.4%). MS (ESI) m/z 496.3 [M+H]$^+$

Example 16

2-(4-(1H-pyrazol-1-yl)benzyl)-7-isobutyl-5-methyl-3-(phenylamino)-2H-pyrazolo-[3,4-d]pyrimidine-4,6(5H,7H)-dione

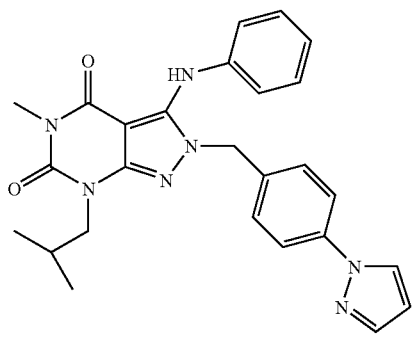 [SMILES: CC(C)Cn1c(=O)n(C)c(=O)c2c(Nc3ccccc3)n(Cc3ccc(-n4cccn4)cc3)nc21]

The synthesis method is analogous to example 1 wherein 1-(4-(bromomethyl)phenyl)-1H-pyrazole is added in step (f) instead of/?-biphenylmethyl bromide. MS (ESI) m/z 470.1 [M+H]+

Example 17

2-(4-(1H-1,2,4-triazol-1-yl)benzyl)-7-isobutyl-5-methyl-3-(phenylamino)-2H-pyrazolo pyrimidine-4,6(5H,7H)-dione

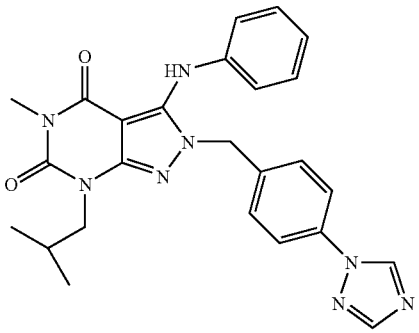 [SMILES: CC(C)Cn1c(=O)n(C)c(=O)c2c(Nc3ccccc3)n(Cc3ccc(-n4cncn4)cc3)nc21]

The synthesis method is analogous to example 1 wherein 1-(4-(bromomethyl)phenyl)-1H-1,2,4-triazole is added in step (f) instead of p-biphenylmethyl bromide (Yield: 89.2%). MS (ESI) m/z 471.1 [M+H]+

Example 18

4-((7-isobutyl-5-methyl-4,6-dioxo-3-(phenylamino)-4,5,6,7-tetrahydropyrazolo[3,4-d]pyrimidin-2-yl)methyl)benzamide

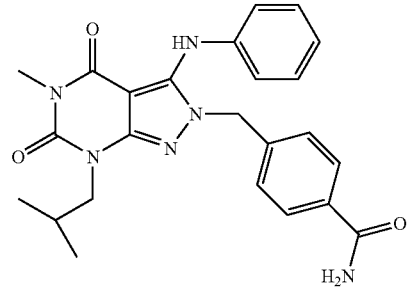 [SMILES: CC(C)Cn1c(=O)n(C)c(=O)c2c(Nc3ccccc3)n(Cc3ccc(C(N)=O)cc3)nc21]

The synthesis method is analogous to example 1 wherein 4-(chloromethyl)benzamide is added in step (f) instead of p-biphenylmethyl bromide. MS (ESI) m/z 447.1 [M+H]+

Example 19

7-isobutyl-5-methyl-2-(4-(methylsulfonyl)benzyl)-3-(phenylamino)-2H-pyrazolo[3,4-d]pyrimidine-4,6(5H,7H)-dione

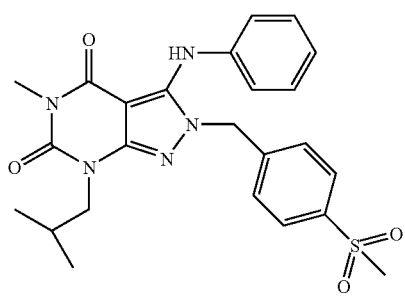 [SMILES: CC(C)Cn1c(=O)n(C)c(=O)c2c(Nc3ccccc3)n(Cc3ccc(S(C)(=O)=O)cc3)nc21]

The synthesis method is analogous to example 1 wherein 1-(bromomethyl)-4-(methylsulfonyl)benzene is added in step (f) instead of p-biphenylmethyl bromide. MS (ESI) m/z 482.1 [M+H]+

Example 20

7-isobutyl-5-methyl-2-(4-(5-methyl-1,2,4-oxadiazol-3-yl)benzyl)-3-(phenylamino)-2H-pyrazolo[3,4-d]pyrimidine-4,6(5H,7H)-dione

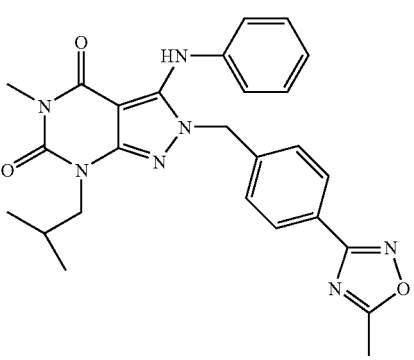 [SMILES: Cc1nc(-c2ccc(Cn3nc4c(c3Nc3ccccc3)c(=O)n(C)c(=O)n4CC(C)C)cc2)no1]

The synthesis method is analogous to example 1 wherein 3-(4-(bromomethyl)phenyl)-5-methyl-1,2,4-oxadiazole is added in step (f) instead of p-biphenylmethyl bromide. MS (ESI) m/z 486.1 [M+H]+

Example 21

2-(4-(5-fluoropyrimidin-2-yl)benzyl)-7-isobutyl-5-methyl-3-(phenylamino)-2H-pyrazolo[3,4-d]pyrimidine-4,6(5H,7H)-dione

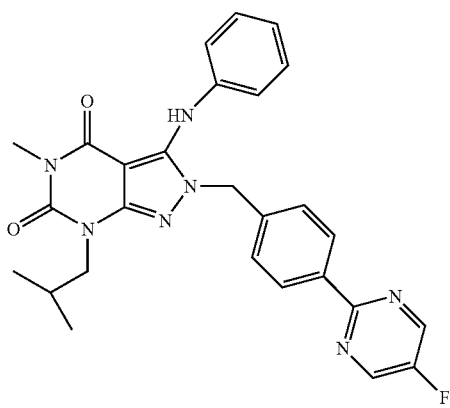 [SMILES: CC(C)Cn1c(=O)n(C)c(=O)c2c(Nc3ccccc3)n(Cc3ccc(-c4ncc(F)cn4)cc3)nc21]

The synthesis method is analogous to example 1 wherein 2-(4-(bromomethyl)phenyl)-5-fluoropyrimidine is added in step (f) instead of p-biphenylmethyl bromide. MS (ESI) m/z 500.0 [M+H]$^+$

Example 22

5-methyl-3-(phenylamino)-2-(4-(pyridin-2-yl)benzyl)-7-((tetrahydrofuran-2-yl)methyl)-2H-pyrazolo[3,4-d]pyrimidine-4,6(5H,7H)-dione

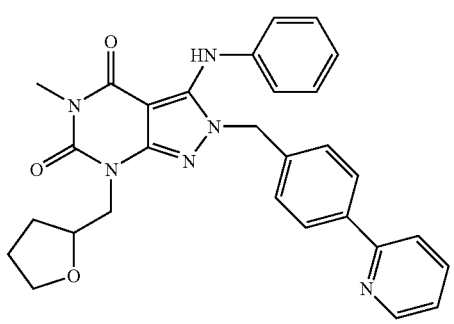 [SMILES: Cn1c(=O)c2c(Nc3ccccc3)n(Cc3ccc(-c4ccccn4)cc3)nc2n(CC2CCCO2)c1=O]

The synthesis method is analogous to example 7 wherein 2-(bromomethyl)-tetrahydrofuran is added instead of iodocyclopentane. MS (ESI) m/z 509.2 [M+H]$^+$

Example 23

5-methyl-7-neopentyl-3-(phenylamino)-2-((6-(trifluoromethyl)pyridin-3-yl)methyl)-2H-pyrazolo[3,4-d]pyrimidine-4,6(5H,7H)-dione

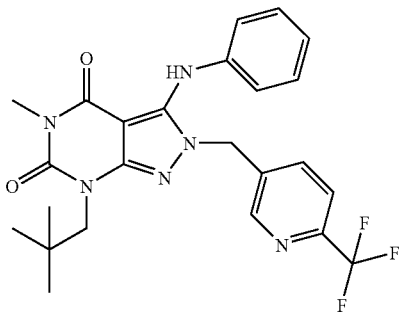 [SMILES: Cn1c(=O)c2c(Nc3ccccc3)n(Cc3ccc(C(F)(F)F)nc3)nc2n(CC(C)(C)C)c1=O]

The synthesis method is analogous to example 1 wherein 1-iodo-2,2-dimethylpropane is added in step (c) instead of isobutyl iodide; and 5-(bromomethyl)-2-(trifluoromethyl)pyridine is added in step (f) instead of p-biphenylmethyl bromide. MS (ESI) m/z 487.2 [M+H]$^+$

Example 24

3-(4-fluorobenzylamino)-7-isobutyl-5-methyl-2-(4-(trifluoromethyl)benzyl)-2H-pyrazolo[3,4-d]pyrimidine-4,6(5H,7H)-dione

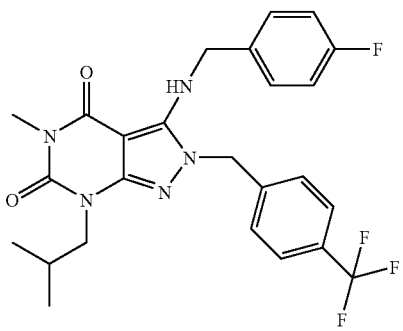 [SMILES: CC(C)Cn1c(=O)n(C)c(=O)c2c(NCc3ccc(F)cc3)n(Cc3ccc(C(F)(F)F)cc3)nc21]

The synthesis method is analogous to example 7 wherein 3-(4-fluorobenzylamino)-5-methyl-2-(4-(trifluoromethyl)benzyl)-2H-pyrazolo[3,4-d]pyrimidine-4,6(5H,7H)-dione is used instead of 5-methyl-3-(phenylamino)-2-(4-(pyridin-2-yl)benzyl)-2H-pyrazolo[3,4-d]pyrimidine-4,6(5H,7H)-dione, and isobutyl iodide is added instead of iodocyclopentane. MS (ESI) m/z 490.2 [M+H]$^+$

Example 25

Measurement of PDE1B Inhibition In Vitro Using IMAP Phosphodiesterase Assay Kit

Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Amp).

A decrease in GMP concentration, measured as decreased Amp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

Example 26

PDE1 Inhibitor Effect on Sexual Response in Female Rats

The effect of PDE1 inhibitors on Lordosis Response in female rats is measured as described in Mani, et al., Science (2000) 287: 1053. Ovariectomized and cannulated wild-type rats are primed with 2 μg estrogen followed 24 hours later by intracerebroventricular (icv) injection of progesterone (2 μg), PDE1 inhibitors of the present invention (0.1 mg, 1.0 mg or 2.5 mg) or sesame oil vehicle (control). The rats are tested for lordosis response in the presence of male rats. Lordosis response is quantified by the lordosis quotient (LQ=number of lordosis/10 mounts×100). The LQ for estrogen-primed female rats receiving compounds 1 or 2, even at 0.1 mg, is over 75, similar to estrogen-primed rats receiving progesterone and significantly higher (p<0.001) than for estrogen-primed rats receiving vehicle.

What is claimed is:

1. The compound of formula I

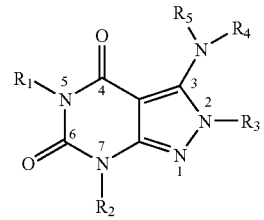

Formula I wherein:
(i) $R_1$ is H or alkyl;
(ii) $R_2$ is H, alkyl, cycloalkyl, haloalkyl, alkylaminoalkyl, hydroxyalkyl, arylalkyl, heteroarylalkyl, or alkoxyarylalkyl;
(iii) $R_3$ is heteroarylmethyl or formula A

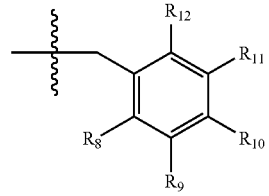

Formula A wherein X, Y and Z are, independently, N or C, and $R_8$, $R_9$, $R_{11}$ and $R_{12}$ are independently H or halogen; and $R_{10}$ is halogen, alkyl, cycloalkyl, haloalkyl, aryl, heteroaryl, alkyl sulfonyl, arylcarbonyl, heteroarylcarbonyl, alkoxycarbonyl, or aminocarbonyl;
(iv) $R_4$ is aryl or heteroaryl; and
(v) $R_5$ is H, alkyl, cycloalkyl, heteroaryl, aryl, p-benzylaryl;
provided that when X, Y or Z is nitrogen, $R_8$, $R_9$ or $R_{10}$, respectively, is not present;
wherein "alk" or "alkyl" refers to $C_{1-6}$ alkyl and "cycloalkyl" refers to $C_{3-6}$ cycloalkyl, in free, salt or physiologically hydrolysable and acceptable ester prodrug form.

2. The compound of Formula II

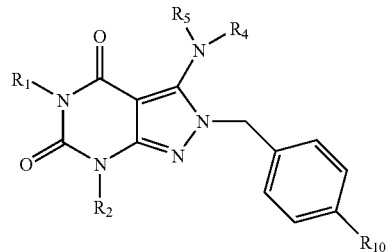

Formula II wherein
$R_1$ is methyl;
$R_2$ is H, alkyl, cycloalkyl, heteroaryl, aryl, haloalkyl, alkylaminoalkyl, hydroxyalkyl, arylalkyl, or alkoxyarylalkyl;
$R_4$ is phenyl;
$R_5$ is H; and R₁₀ is phenyl, pyridyl, pyrimidinyl, pyrazolyl, thiadiazolyl, haloalkyl, alkylsulfonyl, oxadiazolyl, aminocarbonyl, or triazolyl;

wherein "alk" or "alkyl" refers to $C_{1-6}$ alkyl and "cycloalkyl" refers to $C_{3-6}$ cycloalkyl;

in free, salt or physiologically hydrolysable and acceptable ester prodrug form.

3. The compound selected from a group consisting of:
a. 2-(Biphenyl-4-ylmethyl)-7-isobutyl-5-methyl-3-(phenylamino)-2H-pyrazolo[3,4-d]pyrimidine-4,6(5H,7H)-dione;
b. 2-(Biphenyl-4-ylmethyl)-7-(4-methoxybenzyl)-5-methyl-3-(phenylamino)-2H-pyrazolo[3,4-d]pyrimidine-4,6(5H,7H)-dione;
c. 2-(Biphenyl-4-ylmethyl)-3-((biphenyl-4-ylmethyl)(phenyl)amino)-7-(4-methoxybenzyl)-5-methyl-2H-pyrazolo[3,4-d]pyrimidine-4,6(5H,7H)-dione;
d. 7-(4-Methoxybenzyl)-5-methyl-3-(phenylamino)-2-(4-(trifluoromethyl)benzyl)-2H-pyrazolo[3,4-d]pyrimidine-4,6(5H,7H)-dione;
e. 7-(4-Methoxybenzyl)-5-methyl-3-(phenylamino)-2-(4-(pyridin-2-yl)benzyl)-2H-pyrazolo[3,4-d]pyrimidine-4,6(5H,7H)-dione;
f. 5-Methyl-3-(phenylamino)-2-(4-(pyridin-2-yl)benzyl)-2H-pyrazolo[3,4-d]pyrimidine-4,6(5H,7H)-dione;
g. 7-Cyclopentyl-5-methyl-3-(phenylamino)-2-(4-(pyridin-2-yl)benzyl)-2H-pyrazolo[3,4-d]pyrimidine-4,6(5H,7H)-dione;
h. 3-(Cyclopentyl(phenyl)amino)-5-methyl-2-(4-(pyridin-2-yl)benzyl)-2H-pyrazolo[3,4-d]pyrimidine-4,6(5H,7H)-dione;
i. 7-Isobutyl-5-methyl-3-(phenylamino)-2-(4-(pyridin-2-yl)benzyl)-2H-pyrazolo[3,4-d]pyrimidine-4,6(5H,7H)-dione;
j. 7-Cyclohexyl-5-methyl-3-(phenylamino)-2-(4-(pyridin-2-yl)benzyl)-2H-pyrazolo[3,4-d]pyrimidine-4,6(5H,7H)-dione;
k. 5-Methyl-7-neopentyl-3-(phenylamino)-2-(4-(pyridin-2-yl)benzyl)-2H-pyrazolo[3,4-d]pyrimidine-4,6(5H,7H)-dione;
l. (S)-5-Methyl-7-(2-methylbutyl)-3-(phenylamino)-2-(4-(pyridin-2-yl)benzyl)-2H-pyrazolo[3,4-d]pyrimidine-4,6(5H,7H)-dione;
m. 5-Methyl-3-(phenylamino)-2-(4-(pyridin-2-yl)benzyl)-7-(2,2,2-trifluoroethyl)-2H-pyrazolo[3,4-d]pyrimidine-4,6(5H,7H)-dione;
n. (R)-7-(3-Hydroxy-2-methylpropyl)-5-methyl-3-(phenylamino)-2-(4-(pyridin-2-yl)benzyl)-2H-pyrazolo[3,4-d]pyrimidine-4,6(5H,7H)-dione;
o. 7-(2-(Dimethylamino)ethyl)-5-methyl-3-(phenylamino)-2-(4-(pyridin-2-yl)benzyl)-2H-pyrazolo[3,4-d]pyrimidine-4,6(5H,7H)-dione;
p. 2-(4-(1H-pyrazol-1-yl)benzyl)-7-isobutyl-5-methyl-3-(phenylamino)-2H-pyrazolo[3,4-d]pyrimidine-4,6(5H,7H)-dione;
q. 2-(4-(1H-1,2,4-triazol-1-yl)benzyl)-7-isobutyl-5-methyl-3-(phenylamino)-2H-pyrazolo[3,4-d]pyrimidine-4,6(5H,7H)-dione;
r. 4-((7-isobutyl-5-methyl-4,6-dioxo-3-(phenylamino)-4,5,6,7-tetrahydropyrazolo[3,4-d]pyrimidin-2-yl)methyl)benzamide;
s. 7-isobutyl-5-methyl-2-(4-(methylsulfonyl)benzyl)-3-(phenylamino)-2H-pyrazolo[3,4-d]pyrimidine-4,6(5H,7H)-dione;
t. 7-isobutyl-5-methyl-2-(4-(5-methyl-1,2,4-oxadiazol-3-yl)benzyl)-3-(phenylamino)-2H-pyrazolo[3,4-d]pyrimidine-4,6(5H,7H)-dione;
u. 2-(4-(5-fluoropyrimidin-2-yl)benzyl)-7-isobutyl-5-methyl-3-(phenylamino)-2H-pyrazolo[3,4-d]pyrimidine-4,6(5H,7H)-dione;
v. 5-methyl-3-(phenylamino)-2-(4-(pyridin-2-yl)benzyl)-7-((tetrahydrofuran-2-yl)methyl)-2H-pyrazolo[3,4-d]pyrimidine-4,6(5H,7H)-dione;
w. 5-methyl-7-neopentyl-3-(phenylamino)-2-((6-(trifluoromethyl)pyridin-3-yl)methyl)-2H-pyrazolo[3,4-d]pyrimidine-4,6(5H,7H)-dione; and
x. 3-(4-fluorobenzylamino)-7-isobutyl-5-methyl-2-(4-(trifluoromethyl)benzyl)-2H-pyrazolo[3,4-d]pyrimidine-4,6(5H,7H)-dione;

in free, salt or physiologically hydrolysable and acceptable ester prodrug form.

4. A pharmaceutical composition comprising the compound according to claim 1, in free, pharmaceutically acceptable salt or physiologically hydrolysable and acceptable ester prodrug form, in admixture with a pharmaceutically acceptable diluent or carrier.

5. A method of making a compound according to claim 1 comprising reacting a pyrazolo[3,4-d]pyrimidine-4,6(5H,7H)-dione having the Formula (IIIc)

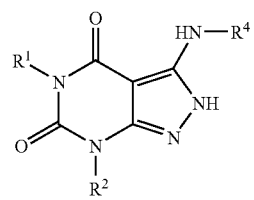

wherein R₁, R₂, and R₄ are as defined in claim 1 for Formula I, with a compound of formula X—R₃ wherein X is a leaving group and R₃ is heteroarylmethyl or Formula A as defined in claim 1, and isolating the compound according to claim 1.

6. The method of claim 5, wherein the reaction is under basic condition.

7. A method of making a compound according to claim 1 comprising reacting a pyrazolo[3,4-d]pyrimidine-4,6(5H,7H)-dione of formula (IIh)

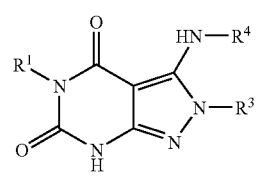

wherein R₁, R₃, and R₄ are as defined in claim 1 for Formula I, with a compound of formula X—R₂ wherein X is a leaving group and R₂ is as defined in claim 1 for Formula I, and isolating the compound according to claim 1.

8. The method of claim 7 wherein the reaction is under basic condition.

9. The compound according to claim 1, wherein R₂ is alkyl in free or salt form, and wherein "alk" or "alkyl" refers to $C_{1-6}$ alkyl.

10. The compound according to claim 1, wherein R₂ is isobutyl in free or salt form.

11. The compound according to claim 1, wherein $R_2$ is hydroxyalkyl in free, salt or physiologically hydrolysable and acceptable ester prodrug form, and wherein "alk" or "alkyl" refers to $C_{1-6}$ alkyl.

12. The compound according to claim 1, wherein $R_2$ is 3-hydroxy-2-methylpropyl in free, salt or physiologically hydrolysable and acceptable ester prodrug form.

13. The compound according to claim 1, wherein $R_3$ is substituted benzyl of formula A

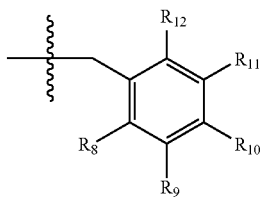

Formula A in free, salt or physiologically hydrolysable and acceptable ester prodrug form, wherein $R_8$, $R_9$, $R_{11}$ and $R_{12}$ are independently H or halogen; and $R_{10}$ is halogen, alkyl, cycloalkyl, haloalkyl, aryl, heteroaryl, arylcarbonyl, heteroarylcarbonyl, alkoxycarbonyl, or aminocarbonyl, and wherein "alk" or "alkyl" refers to $C_{1-6}$ alkyl and "cycloalkyl" refers to $C_{3-6}$ cycloalkyl.

14. The compound according to claim 1, wherein $R_{10}$ is pyridyl in free, salt or physiologically hydrolysable and acceptable ester prodrug form.

15. The compound according to claim 1, wherein $R_4$ is aryl in free, salt or physiologically hydrolysable and acceptable ester prodrug form.

16. The compound according to claim 1, wherein $R_4$ is phenyl in free, salt or physiologically hydrolysable and acceptable ester prodrug form.

17. The compound according to claim 1, wherein $R_5$ is H in free, salt or physiologically hydrolysable and acceptable ester prodrug form.

18. The compound according to claim 1, wherein $R_4$ is phenyl and $R_5$ is H, in free, salt or physiologically hydrolysable and acceptable ester prodrug form.

19. The compound according to claim 1, wherein said compound is (R)-7-(3-Hydroxy-2-methylpropyl)-5-methyl-3-(phenylamino)-2-(4-(pyridin-2-yl)benzyl)-2H-pyrazolo[3,4-d]pyrimidine-4,6(5H,7H)-dione, in free, salt or physiologically hydrolysable and acceptable ester prodrug form.

20. The compound according to claim 1, wherein said compound is 7-Isobutyl-5-methyl-3-(phenylamino)-2-(4-(pyridin-2-yl)benzyl)-2H-pyrazolo[3,4-d]pyrimidine-4,6 (5H,7H)-dione, in free or salt form.

21. The pharmaceutical composition according to claim 4, wherein said compound is a compound of Formula I

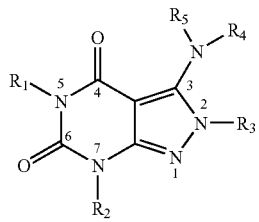

Formula I (i) $R_1$ is H or alkyl;
(ii) $R_2$ is H, alkyl, cycloalkyl, haloalkyl, alkylaminoalkyl, hydroxyalkyl, arylalkyl, heteroarylalkyl, or alkoxyarylalkyl;

(iii) $R_3$ is heteroarylmethyl or a substituted benzyl of formula A

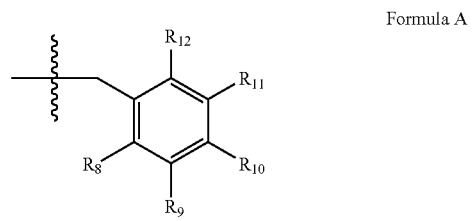

Formula A wherein X, Y and Z are, C, and $R_8$, $R_9$, $R_{11}$ and $R_{12}$ are independently H or halogen; and $R_{10}$ is halogen, alkyl, cycloalkyl, haloalkyl, aryl, heteroaryl, alkyl sulfonyl, arylcarbonyl, heteroarylcarbonyl, alkoxycarbonyl, or aminocarbonyl;

(iv) $R_4$ is aryl or heteroaryl; and (v) $R_5$ is H, alkyl, cycloalkyl, heteroaryl, aryl, p-benzylaryl;

wherein "alk" or "alkyl" refers to $C_{1-6}$ alkyl and "cycloalkyl" refers to $C_{1-6}$ cycloalkyl;

in free, pharmaceutically acceptable salt or physiologically hydrolysable and acceptable ester prodrug form.

22. A pharmaceutical composition comprising the compound according to claim 2, in free, pharmaceutically acceptable salt or physiologically hydrolysable and acceptable ester prodrug form, in admixture with a pharmaceutically acceptable diluent or carrier.

23. A pharmaceutical composition comprising the compound selected from a group consisting of:

a. 2-(Biphenyl-4-ylmethyl)-7-isobutyl-5-methyl-3-(phenylamino)-2H-pyrazolo[3,4-d]pyrimidine-4,6(5H,7H)-dione;

b. 2-(Biphenyl-4-ylmethyl)-7-(4-methoxybenzyl)-5-methyl-3-(phenylamino)-2H-pyrazolo[3,4-d]pyrimidine-4,6(5H,7H)-dione;

c. 2-(Biphenyl-4-ylmethyl)-3-((biphenyl-4-ylmethyl)(phenyl)amino)-7-(4-methoxybenzyl)-5-methyl-2H-pyrazolo[3,4-d]pyrimidine-4,6(5H,7H)-dione;

d. 7-(4-Methoxybenzyl)-5-methyl-3-(phenylamino)-2-(4-(trifluoromethyl)benzyl)-2H-pyrazolo[3,4-d]pyrimidine-4,6(5H,7H)-dione;

e. 7-(4-Methoxybenzyl)-5-methyl-3-(phenylamino)-2-(4-(pyridin-2-yl)benzyl)-2H-pyrazolo[3,4-d]pyrimidine-4,6(5H,7H)-dione;

f. 5-Methyl-3-(phenylamino)-2-(4-(pyridin-2-yl)benzyl)-2H-pyrazolo[3,4-d]pyrimidine-4,6(5H,7H)-dione;

g. 7-Cyclopentyl-5-methyl-3-(phenylamino)-2-(4-(pyridin-2-yl)benzyl)-2H-pyrazolo[3,4-d]pyrimidine-4,6 (5H,7H)-dione;

h. 3-(Cyclopentyl(phenyl)amino)-5-methyl-2-(4-(pyridin-2-yl)benzyl)-2H-pyrazolo[3,4-d]pyrimidine-4,6(5H, 7H)-dione;

i. 7-Isobutyl-5-methyl-3-(phenylamino)-2-(4-(pyridin-2-yl)benzyl)-2H-pyrazolo[3,4-d]pyrimidine-4,6(5H,7H)-dione;

j. 7-Cyclohexyl-5-methyl-3-(phenylamino)-2-(4-(pyridin-2-yl)benzyl)-2H-pyrazolo[3,4-d]pyrimidine-4,6(5H, 7H)-dione;

k. 5-Methyl-7-neopentyl-3-(phenylamino)-2-(4-(pyridin-2-yl)benzyl)-2H-pyrazolo[3,4-d]pyrimidine-4,6(5H,7H)-dione;
l. (S)-5-Methyl-7-(2-methylbutyl)-3-(phenylamino)-2-(4-(pyridin-2-yl)benzyl)-2H-pyrazolo[3,4-d]pyrimidine-4,6(5H,7H)-dione;
m. 5-Methyl-3-(phenylamino)-2-(4-(pyridin-2-yl)benzyl)-7-(2,2,2-trifluoroethyl)-2H-pyrazolo[3,4-d]pyrimidine-4,6(5H,7H)-dione;
n. (R)-7-(3-Hydroxy-2-methylpropyl)-5-methyl-3-(phenylamino)-2-(4-(pyridin-2-yl)benzyl)-2H-pyrazolo[3,4-d]pyrimidine-4,6(5H,7H)-dione;
o. 7-(2-(Dimethylamino)ethyl)-5-methyl-3-(phenylamino)-2-(4-(pyridin-2-yl)benzyl)-2H-pyrazolo[3,4-d]pyrimidine-4,6(5H,7H)-dione;
p. 2-(4-(1H-pyrazol-1-yl)benzyl)-7-isobutyl-5-methyl-3-(phenylamino)-2H-pyrazolo[3,4-d]pyrimidine-4,6(5H,7H)-dione;
q. 2-(4-(1H-1,2,4-triazol-1-yl)benzyl)-7-isobutyl-5-methyl-3-(phenylamino)-2H-pyrazolo[3,4-d]pyrimidine-4,6(5H,7H)-dione;
r. 4-((7-isobutyl-5-methyl-4,6-dioxo-3-(phenylamino)-4,5,6,7-tetrahydropyrazolo[3,4-d]pyrimidin-2-yl)methyl)benzamide;
s. 7-isobutyl-5-methyl-2-(4-(methylsulfonyl)benzyl)-3-(phenylamino)-2H-pyrazolo[3,4-d]pyrimidine-4,6(5H,7H)-dione;
t. 7-isobutyl-5-methyl-2-(4-(5-methyl-1,2,4-oxadiazol-3-yl)benzyl)-3-(phenylamino)-2H-pyrazolo[3,4-d]pyrimidine-4,6(5H,7H)-dione;
u. 2-(4-(5-fluoropyrimidin-2-yl)benzyl)-7-isobutyl-5-methyl-3-(phenylamino)-2H-pyrazolo[3,4-d]pyrimidine-4,6(5H,7H)-dione;
v. 5-methyl-3-(phenylamino)-2-(4-(pyridin-2-yl)benzyl)-7-((tetrahydrofuran-2-yl)methyl)-2H-pyrazolo[3,4-d]pyrimidine-4,6(5H,7H)-dione;
w. 5-methyl-7-neopentyl-3-(phenylamino)-2-((6-(trifluoromethyl)pyridin-3-yl)methyl)-2H-pyrazolo[3,4-d]pyrimidine-4,6(5H,7H)-dione; and
x. 3-(4-fluorobenzylamino)-7-isobutyl-5-methyl-2-(4-(trifluoromethyl)benzyl)-2H-pyrazolo[3,4-d]pyrimidine-4,6(5H,7H)-dione;

in free, pharmaceutically acceptable salt or physiologically hydrolysable and acceptable ester prodrug form, in admixture with a pharmaceutically acceptable diluent or carrier.

24. The pharmaceutical composition according to claim 4, wherein said compound is (R)-7-(3-Hydroxy-2-methylpropyl)-5-methyl-3-(phenylamino)-2-(4-(pyridin-2-yl)benzyl)-2H-pyrazolo[3,4-d]pyrimidine-4,6(5H,7H)-dione, in free, pharmaceutically acceptable salt or physiologically hydrolysable and acceptable ester prodrug form.

25. The pharmaceutical composition according to claim 4, wherein said compound is 7-Isobutyl-5-methyl-3-(phenylamino)-2-(4-(pyridin-2-yl)benzyl)-2H-pyrazolo[3,4-d]pyrimidine-4,6(5H,7H)-dione, in free or pharmaceutically acceptable salt form.

26. The compound according to claim 1, wherein $R_2$ is 2,2-dimethylpropyl in free or salt form.

27. The compound according to claim 1, wherein $R_2$ is p-methoxybenzyl or cyclopentyl, in free or salt form.

28. The compound according to claim 1, wherein $R_{10}$ is pyrazol-1-yl or 1,2,4-triazol-1-yl, in free, salt or physiologically hydrolysable and acceptable ester prodrug form.

29. The compound according to claim 1 selected from a group consisting of:

7-(4-Methoxybenzyl)-5-methyl-3-(phenylamino)-2-(4-(pyridin-2-yl)benzyl)-2H-pyrazolo[3,4-d]pyrimidine-4,6(5H,7H)-dione;

7-Cyclopentyl-5-methyl-3-(phenylamino)-2-(4-(pyridin-2-yl)benzyl)-2H-pyrazolo[3,4-d]pyrimidine-4,6(5H,7H)-dione;

7-Isobutyl-5-methyl-3-(phenylamino)-2-(4-(pyridin-2-yl)benzyl)-2H-pyrazolo[3,4-d]pyrimidine-4,6(5H,7H)-dione;

5-Methyl-7-neopentyl-3-(phenylamino)-2-(4-(pyridin-2-yl)benzyl)-2H-pyrazolo[3,4-d]pyrimidine-4,6(5H,7H)-dione;

7-(2-(Dimethylamino)ethyl)-5-methyl-3-(phenylamino)-2-(4-(pyridin-2-yl)benzyl)-2H-pyrazolo[3,4-d]pyrimidine-4,6(5H,7H)-dione; and 2-(4-(1H-pyrazol-1-yl)benzyl)-7-isobutyl-5-methyl-3-(phenylamino)-2H-pyrazolo[3,4-d]pyrimidine-4,6(5H,7H)-dione, in free or salt form.

* * * * *